United States Patent
Kikuchi et al.

(10) Patent No.: US 6,558,316 B2
(45) Date of Patent: May 6, 2003

(54) ENDOSCOPE OPTICAL SYSTEM INCLUDING COMPOSITION HAVING DURABILITY TO A STERILIZATION TREATMENT

(75) Inventors: Akira Kikuchi, Hachioji (JP); Sayaka Konno, Hino (JP); Hiroaki Kinoshita, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/891,384

(22) Filed: Jun. 27, 2001

(65) Prior Publication Data

US 2003/0040422 A1 Feb. 27, 2003

(51) Int. Cl.$^7$ .............................. A61B 1/00; C03C 3/253
(52) U.S. Cl. ....................... 600/133; 600/160; 600/162; 600/176; 501/42; 501/51
(58) Field of Search ................................. 600/160, 162, 600/169, 176, 133; 501/37, 42, 49–52, 64, 65, 78

(56) References Cited

U.S. PATENT DOCUMENTS

| | | | | |
|---|---|---|---|---|
| 3,955,991 A | * | 5/1976 | Young et al. | 252/625 |
| 4,120,732 A | * | 10/1978 | Komorita et al. | 501/42 |
| 4,166,746 A | * | 9/1979 | Ishibashi et al. | 501/42 |
| 5,188,094 A | * | 2/1993 | Adair | 359/512 |
| 5,457,576 A | * | 10/1995 | Atkinson et al. | 359/435 |
| 5,472,471 A | * | 12/1995 | Baba et al. | 501/10 |
| 5,536,244 A | * | 7/1996 | Muller et al. | 228/124.1 |
| 6,038,079 A | | 3/2000 | Michaels | |
| 6,328,691 B1 | * | 12/2001 | Rudischhauser | 600/133 |

* cited by examiner

Primary Examiner—John P. Leubecker
(74) Attorney, Agent, or Firm—Armstrong, Westerman & Hattori, LLP

(57) ABSTRACT

A composition has a durability to a sterilization treatment using vapor under high temperature and pressure and capable of transmitting or absorbing light. The composition comprises a group A including 15 to 23 mol % of lanthanum oxide, 3 to 8 mol % of gadolinium oxide, 3 to 8 mol % of tantalum oxide, and 8 mol % or less of yttrium oxide; a group B including 30 to 45 mol % of boron oxide, 20 mol % or less of silicon oxide, and 20 mol % or less of germanium oxide; zero mol % of alkaline metal oxide or alkaline earth metal oxide; and a group D including 0.3 to 15 mol % of niobium oxide and 3 to 15 mol % of zirconium oxide. A mol % ratio A/B between the group A and group B is 80% or more, and a dissolving-out rate of metal ion of the composition is $0.002 \times 10^{-6}$ mol/hour or less per square centimeter. In case of applying the composition to an endoscope including an observation system and an illuminating system, an optical element disposed at the outer surface of the observation system and an optical element disposed at the outer surface of the illuminating system are formed of the composition.

20 Claims, 15 Drawing Sheets

210

211

ENDOSCOPE OPTICAL SYSTEM INCLUDING COMPOSITION HAVING DURABILITY TO A STERILIZATION TREATMENT

FIELD OF THE INVENTION

The present invention relates to a composition excellent in durability to a sterilization process and an endoscope optical system using the composition.

BACKGROUND OF THE INVENTION

The durability to the sterilization process or treatment herein includes a durability under harsh conditions, for example, to so-called autoclave sterilization using saturated vapor under high temperature and pressure at about 140° C. In these years, the autoclave sterilization involving the harsh conditions has been dominant in endoscopes which are required to be rinsed out, disinfected, and sterilized after use.

In disinfection treatments using chemicals, even if an ordinary optical glass is used for an endoscope, such a glass has no possibility of suffering from corrosion which leads to deteriorated opacity and light transmittance, because the condition of this treatment is not so harsh. In contrast, the harsh condition of the autoclave sterilization causes undesirable corrosion of the optical glass, resulting in deteriorated opacity and inability to illuminate or observe. On the other hand, no chemicals are used in the autoclave sterilization. Thus, the autoclave sterilization is not harmful to the environment and excellent in economical efficiency.

Sapphire has been known as an optical material having an excellent corrosion resistance under any harsh conditions. U.S. Pat. No. 6,038,079 discloses an example of applying sapphire to an optical system of an endoscope. In this patent, sapphire is used in a part or all of lenses for the objective optical system at the front end of the endoscope.

While sapphire advantageously has an excellent durability under harsh conditions as described above, it has the following disadvantages.
1) The high material cost of sapphire leads to a high product cost.
2) The high hardness of sapphire requires a long time for polishing to process it into an optical lens. This is not adequate to mass production.
3) The high: melting temperature of sapphire precludes the possibility of applying a postforming operation in its molten state to process it into an optical lens. This disenables sapphire to process into a complex shape such as an aspheric lens.
4) Sapphire has only one value for each of refractive index and Abbe number in optical properties thereof. Thus, it is difficult to correct an aberration sufficiently in optical design processes, resulting in deteriorated performance of the optical system.

SUMMARY OF THE INVENTION

It is therefore an object of the present invention to provide an improved composition free from the disadvantages of sapphire (in cost, hardness, workability, melting temperature, optical properties, etc) and having a sophisticated durability to a sterilization treatment.

It is another object of the present invention to provide an endoscope using the improved composition in an optical system thereof and having an effective structure capable of yielding a sufficient durability to a sterilization treatment.

In order to achieve the above object, according to the present invention, there is provided a composition having a durability to a sterilization treatment using vapor under high temperature and pressure and capable of transmitting or absorbing light, the composition comprising: a group A including 15 to 23 mol % of lanthanum oxide, 3 to 8 mol % of gadolinium oxide, 3 to 8 mol % of tantalum oxide, and 8 mol % or less of yttrium oxide; a group B including 30 to 45 mol % of boron oxide, 20 mol % or less of silicon oxide, and 20 mol % or less of germanium oxide; zero mol % of alkaline metal oxide or alkaline earth metal oxide; and a group D including 0.3 to 15 mol % of niobium oxide and 3 to 15 mol % of zirconium oxide, wherein a mol % ratio A/B between the group A and group B is 80% or more, and a dissolving-out rate of metal ion of the composition is $0.002 \times 10^{-6}$ mol/hour or less per square centimeter, wherein in case of applying the composition to an endoscope including an observation system and an illuminating system, an optical element disposed at the outer surface of the observation system and an optical element disposed at the outer surface of the illuminating system are formed of the composition.

The objects of the present invention are also achieved by providing a composition having a durability to a sterilization treatment using vapor under high temperature and pressure and capable of transmitting or absorbing light, the composition comprising: a group A including at least either one of lanthanum oxide, gadolinium oxide, tantalum oxide and yttrium oxide, a total mol % of the group A being 25 mol % or more; and a group B including at least either one of boron oxide, silicon oxide and germanium oxide, a total mol % of the group B being 60 mol % or less.

The objects of the present invention are also achieved by providing a composition wherein a mol % ratio A/B between the group A and group B is 80% or more.

The objects of the present invention are also achieved by providing a composition having a durability to a sterilization treatment using vapor under high temperature and pressure and capable of transmitting or absorbing light, the composition comprising: a group A including at least either one of lanthanum oxide, gadolinium oxide, tantalum oxide and yttrium oxide, a total mol % of the group A being 25 mol % or more; a group B including at least either one of boron oxide, silicon oxide and germanium oxide, a total mol % of the group B being 60 mol % or less; and a group C including 5 mol % or less of alkaline metal oxide or alkaline earth metal oxide.

The objects of the present invention are also achieved by providing a composition wherein a mol % ratio A/B between the group A and group B is 80% or more.

The objects of the present invention are also achieved by providing a composition having a durability to a sterilization treatment using vapor under high temperature and pressure and capable of transmitting or absorbing light, the composition comprising: a group A including at least either one of lanthanum oxide, gadolinium oxide, tantalum oxide and yttrium oxide, a total mol % of the group A being 25 mol % or more; a group B including at least either one of boron oxide, silicon oxide and germanium oxide, a total mol % of the group B being 60 mol % or less; and zero mol % of alkaline metal oxide or alkaline earth metal oxide.

The objects of the present invention are also achieved by providing a composition wherein a mol % ratio A/B between the group A and group B is 80% or more.

The objects of the present invention are also achieved by providing a composition having a durability to a sterilization treatment using vapor under high temperature and pressure and capable of transmitting or absorbing light, the composition comprising: a group A including at least either one of lanthanum oxide, gadolinium oxide, tantalum oxide and yttrium oxide, a total mol % of the group A being 25 mol % or more; and a group B including at least boron oxide, a total mol % of the group B being 60 mol % or less, wherein silicon oxide and germanium oxide are not included in the group B.

The objects of the present invention are also achieved by providing a composition wherein a mol % ratio A/B between the group A and group B is 80% or more.

The objects of the present invention are also achieved by providing a composition having a durability to a sterilization treatment using vapor under high temperature and pressure and capable of transmitting or absorbing light, the composition comprising: a group A including at least either one of lanthanum oxide, gadolinium oxide, tantalum oxide and yttrium oxide, a total mol % of the group A being 25 mol % or more; a group B including at least boron oxide, a total mol % of the group B being 60 mol % or less, wherein silicon oxide and germanium oxide are not included in the group B; and zero mol % of alkaline metal oxide or alkaline earth metal oxide.

The objects of the present invention are also achieved by providing a composition wherein a mol % ratio A/B between the group A and group B is 80% or more.

The objects of the present invention are also achieved by providing a composition having a durability to a sterilization treatment using vapor under high temperature and pressure and capable of transmitting or absorbing light, the composition comprising: a group A including at least either one of 13 to 35 mol % of lanthanum oxide, 16 mol % or less of gadolinium oxide, 16 mol % or less of tantalum oxide, and 16 mol % or less of yttrium oxide, a total mol % of the group A being 25 mol % or more; a group B including at least either one of 22 to 60 mol % of boron oxide, 25 mol % or less of silicon oxide, and 25 mol % or less of germanium oxide, a total mol % of the group B being 60 mol % or less; a group C including 5 mol % or less of alkaline metal oxide or alkaline earth metal oxide; and a group D including at least either one of 0.3 to 15 mol % of niobium oxide and 3 to 15 mol % of zirconium oxide.

The objects of the present invention are also achieved by providing a composition wherein a mol % ratio A/B between the group A and group B is 80% or more.

The objects of the present invention are also achieved by providing an endoscope using the composition wherein an optical element disposed at an outer surface of an optical system of the endoscope is formed of the composition.

The objects of the present invention are also achieved by providing an endoscope wherein the optical system includes an observation system and an illuminating system, wherein at least either one of an optical element disposed at the outer surface of the observation system and an optical element disposed at the outer surface of the illuminating system is formed of the composition.

The objects of the present invention are also achieved by providing an endoscope wherein the optical system includes an observation system and an illuminating system, wherein all of an optical element disposed at the outer surface of the observation system and an optical element disposed at the outer surface of the illuminating system are formed of the composition.

The objects of the present invention are also achieved by providing an endoscope using the composition wherein a surface of an optical element disposed at an outer surface of an optical system of the endoscope is formed of the composition.

The objects of the present invention are also achieved by providing an endoscope wherein the optical system includes an observation system and an illuminating system, wherein at least either one of a surface of an optical element disposed at the outer surface of the observation system and a surface of an optical element disposed at the outer surface of the illuminating system is formed of the composition.

The objects of the present invention are also achieved by providing an endoscope wherein the optical system includes an observation system and an illuminating system, wherein all of a surface of an optical element disposed at the outer surface of the observation system and a surface of an optical element disposed at the outer surface of the illuminating system are formed of the composition.

The objects of the present invention are also achieved by providing an endoscope using the composition which includes an objective lens unit for imaging an object on a front end of an insertion section of the endoscope, wherein an optical element located proximal to the object side of the objective lens unit and an optical element located proximal to the image side of the objective lens unit are formed of the composition.

The objects of the present invention are also achieved by providing an endoscope wherein all of optical elements of the objective lens unit are formed of the composition.

The objects of the present invention are also achieved by providing an endoscope wherein the optical element located proximal to the image side of the objective lens unit is a convex lens.

The objects of the present invention are also achieved by providing an endoscope wherein the optical element located proximal to the image side of the objective lens unit is either one of an absorption type infrared cut-off filter and an interference type infrared cut-off filter.

The objects of the present invention are also achieved by providing an endoscope using the composition which includes, in order from the object side of the endoscope, an image guide and an ocular lens unit, wherein an optical element located proximal to the image guide side of the objective lens unit and an optical element located proximal to the observation side of the objective lens unit are formed of the composition.

The objects of the present invention are also achieved by providing an endoscope wherein all of optical elements of the ocular lens unit are formed of the composition.

The objects of the present invention are also achieved by providing an endoscope wherein at least a part of the image guide is formed of the composition.

The objects of the present invention are also achieved by providing an endoscope using the composition which includes an image pickup device for imaging an object on a front end of an insertion section of the endoscope, wherein an optical element located proximal to the object side of the image pickup device is formed of the composition.

The objects of the present invention are also achieved by providing an endoscope using the composition which includes, in order from the object side at a front end of an insertion section of the endoscope, an illuminating unit and a light guide, wherein an optical element located proximal to the object side of the illuminating unit and an optical element located proximal to the light guide side of the illuminating unit are formed of the composition.

The objects of the present invention are also achieved by providing an endoscope wherein all of optical elements of the illuminating unit are formed of the composition.

The objects of the present invention are also achieved by providing an endoscope wherein at least a part of the light guide is formed of the composition.

The objects of the present invention are also achieved by providing an endoscope using the composition which includes, in order from the light source side of the endoscope, an incident unit and a light guide, wherein an optical element located proximal to the light source side of the incident unit and an optical element located proximal to the light guide side of the incident unit are formed of the composition.

The objects of the present invention are also achieved by providing an endoscope wherein all of optical elements of the incident unit are formed of the composition.

The objects of the present invention are also achieved by providing an endoscope, wherein the incident unit includes a columnar rod-shaped optical element, wherein the rod-shaped optical element is formed of the composition.

The objects of the present invention are also achieved by providing a composition having a durability to a sterilization treatment using vapor under high temperature and pressure and capable of transmitting or absorbing light, wherein a dissolving-out rate of metal ion of the composition is $0.002 \times 10^{-6}$ mol/hour or less per square centimeter.

The objects of the present invention are also achieved by providing a composition wherein the dissolving-out rate of metal ion of the composition is $0.0005 \times 10^{-6}$ mol/hour or less per square centimeter.

Other features and advantages of the present invention will be apparent from the accompanying drawings and from the detailed description.

DESCRIPTION OF THE PREFERRED EMBODIMENT

Figure 1:
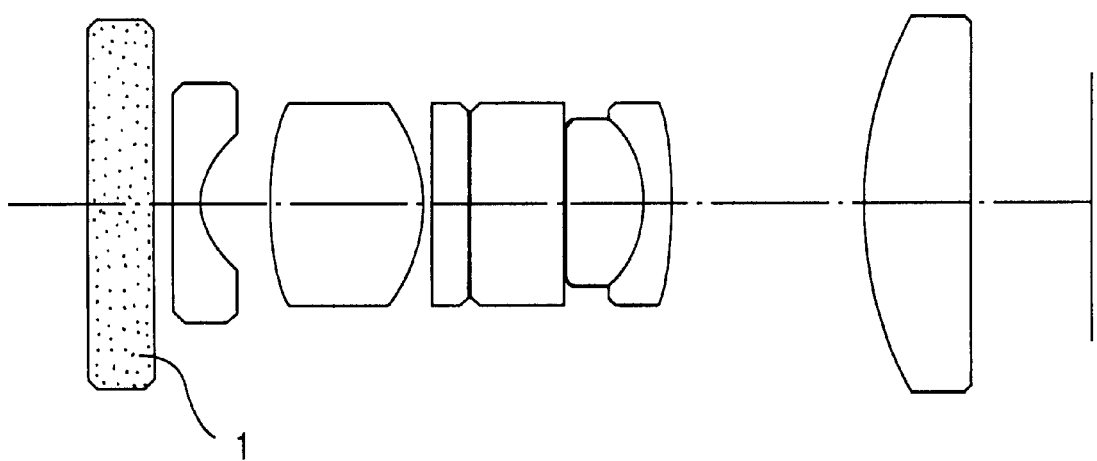
FIG. 1 is a fundamental conceptual view showing an objective optical system according to an embodiment of the present invention.

Table 1 shows examples 1 to 16 of a composition having durability to a sterilization treatment according to the present invention. In Table 1, each ratio of components is defined by mol % based on 100 mol % of oxides.

Raw materials were prepared by oxides, carbonates, nitrates or the like of respective elements, and all of the raw materials were weighed by each given amount to mix with each other in a conventional manner. This mixed powder was fused in a platinum crucible by an electric furnace at 1350° C. to 1450° C. for 1 to 3 hours to homogenize the molten product. Then, the molten product was cooled down to a certain temperature corresponding to a suitable viscosity for casting the molten product. After casting, the distortion of the cast product was eliminated to form an optically homogeneous composition. The obtained composition was processed into an optical lens in a conventional manner (polishing, forming).

The optical lens was applied to an endoscope optical system, and subjected to the autoclave sterilization. One cycle of the autoclave sterilization was conducted under a saturated vapor pressure at the temperature 135° C. for 5 minutes, and after conducting a plurality of cycles, roughness on the surface of each composition was observed by an optical microscope.

A polished optical glass was subjected to 30 cycles of a sterilization treatment in which one cycle of the sterilization treatment was conducted under a saturated vapor pressure at the temperature 135° C. for 250 minutes. During this treatment, dissolving-out components from the glass were sampled to determine each element and amount of the dissolving-out components by inductively coupled mass spectrometry (ICP-MS).

Table 1 shows a result of the autoclave test for each composition of the examples each having a different ratio of a group A to a group B, wherein the group A comprises oxides of rare earth elements consisting of $La_2O_3$, $Gd_2O_3$, $Ta_2O_5$ and $Y_2O_3$, and the group B comprises oxides of creating glass network-former.consisting of $B_2O_3$, $SiO_2$ and $GeO_2$.

TABLE 1

| Example | | 1 | 2 | 3 | 4 | 5 | 6 | 7 | 8 |
|---|---|---|---|---|---|---|---|---|---|
| Refractive index | d-line | 1.95 | 2 | 1.9 | 1.95 | 2.1 | 1.98 | 1.9 | 1.84 |
| Abbe number | d-line | 38 | 36 | 35 | 30 | 40 | 40 | 45 | 45 |
| Autoclave durability | (cycle) | 2000 | 2000 | 2000 | 2000 | 3000 | 2000 | 2000 | 1000 |
| Dissolving-out test | (10-6 mol/cm2 · h) | 0.0002 | 0.0002 | 0.0002 | 0.0002 | 0.0001 | 0.0002 | 0.0002 | 0.0008 |
| Component | $SiO_2$ (mol %) | | | 9.6 | 11.2 | 4.0 | 4.0 | 6.0 | 8.0 |
| | $B_2O_3$ | 46.9 | 28.0 | 39.0 | 26.6 | 22.0 | 35.0 | 34.5 | 50.0 |
| | $GeO_2$ | | | | | | | | |
| | $La_2O_3$ | 25.0 | 31.0 | 25.0 | 27.2 | 34.9 | 27.0 | 25.0 | 23.0 |
| | $Ta_2O_5$ | 11.0 | 16.0 | 7.3 | 11.4 | 16.0 | 11.4 | 8.3 | 4.0 |
| | $Gd_2O_3$ | 8.0 | 14.0 | 8.5 | 11.7 | 14.0 | 11.5 | 9.0 | |
| | $Y_2O_3$ | | | | | | | | 4.3 |
| | $WO_3$ | | | | | | | | |
| | $TiO_2$ | | | 4.0 | 5.0 | | | | |
| | $ZrO_2$ | 7.0 | 8.9 | 3.9 | 4.2 | 7.0 | 9.0 | 14.5 | 8.0 |
| | $Nb_2O_5$ | 1.9 | 1.9 | 2.5 | 2.5 | 1.9 | 1.9 | 2.5 | 2.5 |
| | $Al_2O_3$ | 0.1 | 0.1 | 0.1 | 0.1 | 0.1 | 0.1 | 0.1 | 0.1 |
| | ZnO | | | | | | | | |
| | BaO | | | | | | | | |
| | Li2O | | | | | | | | |
| | $Sb_2O_3$ | 0.1 | 0.1 | 0.1 | 0.1 | 0.1 | 0.1 | 0.1 | 0.1 |
| Total | (mol %) | 100.0 | 100.0 | 100.0 | 100.0 | 100.0 | 100.0 | 100.0 | 100.0 |
| Group A | (mol %) | 44.0 | 61.0 | 40.8 | 50.3 | 64.9 | 49.9 | 42.3 | 31.3 |
| Group B | (mol %) | 46.9 | 28.0 | 48.6 | 37.8 | 26.0 | 39.0 | 40.5 | 58.0 |
| A/B | | 94% | 218% | 84% | 133% | 250% | 128% | 104% | 54% |

| Example | | 9 | 10 | 11 | 12 | 13 | 14 | 15 | 16 |
|---|---|---|---|---|---|---|---|---|---|
| Refractive index | d-line | 1.88 | 1.82 | 1.83 | 2.01 | 1.75 | 1.8 | 2.1 | 1.94 |
| Abbe number | d-line | 40 | 47 | 37 | 28 | 50 | 35 | 25 | 39 |
| Autoclave durability | (cycle) | 1500 | 1000 | 500 | 1000 | 250 | 500 | 1000 | 500 |
| Dissolving-out test | (10-6 mol/cm2 · h) | 0.0005 | 0.0008 | 0.0013 | 0.0008 | 0.002 | 0.0013 | 0.0008 | 0.0013 |
| Component | $SiO_2$ (mol %) | 18.0 | 17.0 | 12.5 | 4.3 | 22.0 | 12.0 | 3.2 | |
| | $B_2O_3$ | 32.0 | 41.0 | 35.0 | 25.0 | 37.0 | 35.0 | 21.2 | 46.5 |
| | $GeO_2$ | | | | 20.4 | | | 25.0 | |
| | $La_2O_3$ | 22.1 | 15.0 | 13.4 | 19.5 | 14.0 | 13.0 | 19.5 | 22.6 |
| | $Ta_2O_5$ | 11.0 | 3.5 | | 4.1 | 6.0 | 1.0 | 5.0 | 11.0 |
| | $Gd_2O_3$ | 8.0 | 14.0 | | | | | | 9.3 |
| | $Y_2O_3$ | | | | | 6.0 | | | |
| | $WO_3$ | | | 1.7 | | | 2.0 | | |
| | $TiO_2$ | | | | 4.1 | | | 6.0 | |
| | $ZrO_2$ | 8.0 | 8.5 | 5.2 | 7.8 | 3.5 | 4.8 | 7.3 | 5.3 |
| | $Nb_2O_5$ | 0.7 | 0.8 | 7.4 | 14.5 | 0.3 | 3.0 | 12.5 | 1.9 |
| | $Al_2O_3$ | 0.1 | 0.1 | 0.1 | 0.2 | 0.1 | 0.1 | 0.2 | 0.1 |
| | ZnO | | | 21.1 | | 4.0 | 26.0 | | |
| | BaO | | | 2.8 | | 3.0 | | | |
| | Li2O | | | 0.7 | | 4.0 | 3.0 | | 3.2 |
| | $Sb_2O_3$ | 0.1 | 0.1 | 0.1 | 0.1 | 0.1 | 0.1 | 0.1 | 0.1 |
| Total | (mol %) | 100.0 | 100.0 | 100.0 | 100.0 | 100.0 | 100.0 | 100.0 | 100.0 |
| Group A | (mol %) | 41.1 | 32.5 | 13.4 | 23.6 | 26.0 | 14.0 | 24.5 | 42.9 |
| Group B | (mol %) | 50.0 | 58.0 | 47.5 | 49.7 | 59.0 | 47.0 | 49.4 | 46.5 |
| A/B | | 82% | 56% | 28% | 47% | 44% | 30% | 50% | 92% |

The composition according to the present invention essentially includes $B_2O_3$ and $La_2O_3$ as primary components. Preferably, the composition includes another substantial component, such as $Ta_2O_5$ or $Gd_2O_3$ to provide high refractive index and enhance autoclave durability, or $ZrO_2$ or $Nb_2O_5$ to stabilize a range of vitrification. In particular, it is preferable to include B-La-Gd-Ta-Zr-Nb series having a stable range of vitrification or B-Si-La-Gd-Ta-Zr-Nb series composed of the B-La-Gd-Ta-Zr-Nb series and $SiO_2$ added for stabilizing vitrification. If necessary, another element, such as $Y_2O_3$, $GeO_2$, $TiO_2$ or $Al_2O_3$, may be included.

As the result of analyzing the dissolving-out components from each composition, the following points have been come into focus. For a glass including alkaline metal element and alkaline earth metal element, these components are liable to dissolve out due to their property apt to be ionized. For a glass including no alkaline metal element and no alkaline earth metal element, Si, Ge and B serving as glass network-former is liable to dissolve out, and rare earth elements such as La and other elements such as Zr do not substantially dissolve out. Among the glass network-former, Si and Ge dissolve out in preference to B.

Based on the above knowledge, it has been concluded that a particular composition including no alkaline glass and no alkaline earth glass, and including a larger amount or ratio of rare earth components and a less amount or ratio of glass network-formers, particularly silicon (Si) and germanium (Ge), would provide an excellent autoclave durability.

For the composition including no alkaline metal element, the autoclave durability of each composition can be assured in the range of about 1000 cycles when the ratio A/B is about 50%, in the range of about 1500 cycles when the ratio A/B is 80% or more, and in the range of about 2000 cycles when the ratio A/B is 100% or more. Thus, the autoclave durability is enhanced as the ratio A/B is increased. In a practical standpoint, an adequate autoclave durability can be obtained from the ratio A/B of 80% (0.8) or more.

A high refractive index of the composition may be obtained by increasing the amount or ratio of rare earth elements, or using $GeO_2$ as a substitute for $B_2O_3$. However, in view of the above result showing that the glass network-formers are hydrolyzed by the vapor, the former approach capable of reducing the ratio of the glass network-formers is more effective.

Other components will be described which may be included in the composition in addition to the primary components. Alkaline element oxides such as $Li_2O$, $Na_2O$, $K_2O$ and $Cs_2O$, or alkaline earth element oxides such as BaO, CaO and SrO significantly deteriorate the durability to the sterilization treatment under high temperature and pressure. Thus, it is preferable to mix these components as less as possible. However, considering that it is necessary to facilitate the vitrification and these oxides are included in the raw materials as inevitable impurities, it is practically required to control the amount of these components in a suitable range not to neutralize the effects of the present invention.

The autoclave durability is determined by and varied depending on the plurality of factors as described above. However, as shown in the examples 11, 14 and 16, when alkaline and alkaline earth metals are included by about 3 mol %, the autoclave durability is deteriorated down to about 500 cycles, and when included by about 6 mol %, the autoclave durability is deteriorated down to about 250 cycles. Thus, the amount of alkaline metal or alkaline earth metal oxides may be 5 mol % or less, preferably 3 mol % or less, more preferably not be included.

As long as having no adverse effect against the present invention, it is apparent that any other elements other than those shown in the above examples may be added as raw materials. For example, $Sb_2O_3$ serving as clarificant for glass, $WO_3$ or $TeO_2$ as a component yielding high refractive index, or fluorine having an effect of improving chemical properties or transmission factor may be included. However, it is desirable not to use PbO or $ThO_2$ as a component yielding high refractive index, or $As_2O_3$ serving as clarificant, because these oxides have significant adverse effects on the environment and on the biocompatibility.

FIG. 1 shows an objective optical system according to a first embodiment of the present invention. According to a fundamental concept of the present invention, an objective cover glass 1 disposed, on the object side of the objective optical system and exposed to the outside air is formed of the composition having the improved durability to the sterilization treatment according to the present invention (hereinafter referred to as "the composition having the improved sterilization durability").

FIGS. 2 to 5 show objective optical systems according to a second to fifth embodiments of the present invention, respectively, and the dimensional data of these objective optical systems are shown in Tables 2 to 5. In Tables 2 to 5, "S" indicates a number of each lens surface, "R" indicating a curvature radius of each lens surface, "D" indicating a thickness of or distance between each lens, "Nd" indicating a refractive index of each lens, and "Vd" indicating an Abbe number of each lens. In all of the above embodiments, a lens 2 located proximal to the object side of the objective optical system and exposed to the outside air is formed of the composition having the improved sterilization durability. These embodiments have differences in types of optical system, respectively, and may be selected depending on the product specification.

The types of optical system will be described as follows. In the following description, "−" (minus) indicates a lens having a negative power, and "+" (plus) indicates a lens having a positive power. The term "lens" herein includes a single lens, a combination of plural single lens, and a cemented lens. For the combination of plural single lens or the cemented lens, the term "power" means a combined or resultant power. An aperture diaphragm is indicated by the symbol "S", an infrared cut-off filter being indicated by the symbol "F", and a cover glass being indicated by the symbol "C".

Figure 2:
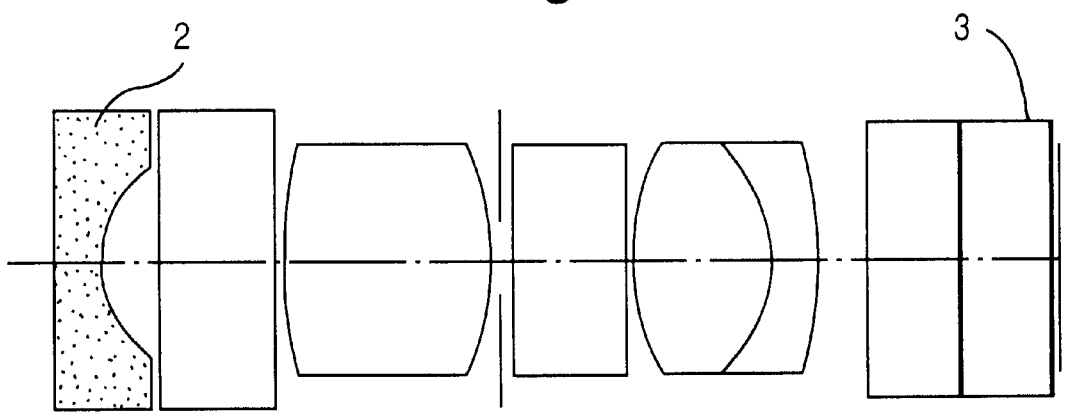
FIGS. 2 to 5 show objective optical systems according to other embodiments of the present invention, respectively.

As shown in FIG. 2, the objective optical system of the second embodiment comprises, in order from the object side, −, F, +, S, F, +, C. An objective cover glass 3 located proximal to the object side of the objective optical system is closely contacted with an image pickup device unit. It is herein defined that this objective cover glass 3 is one of components of the image pickup device unit, and not included in components of the objective optical system.

Figure 3:
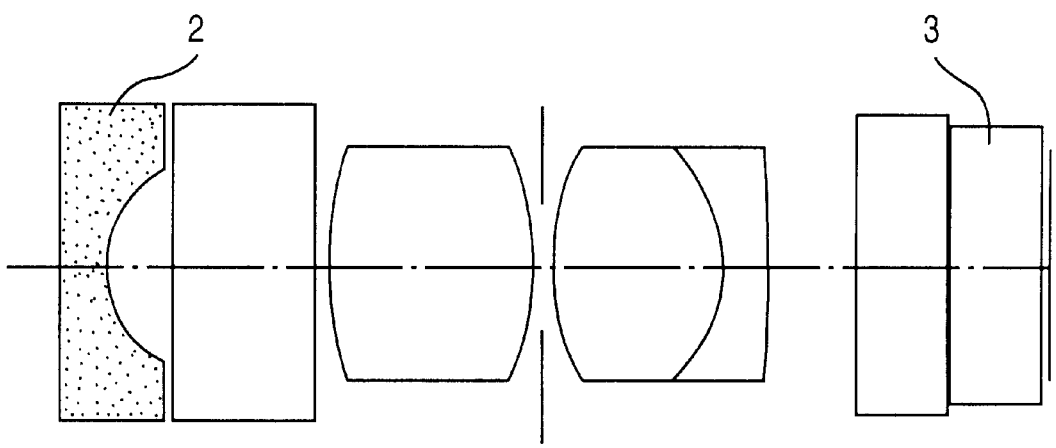
Figure 4:
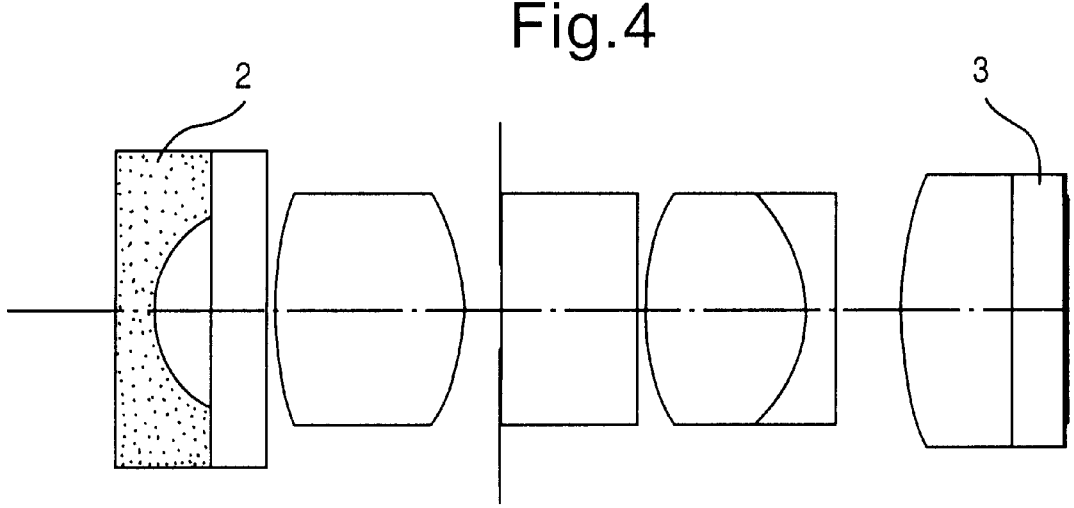
Figure 5:
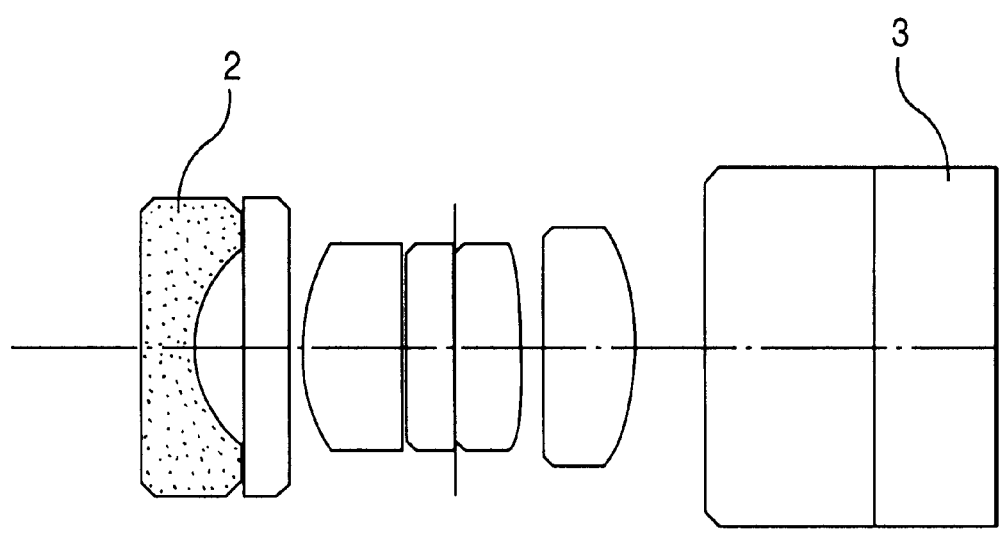

As shown in FIG. 3, the objective optical system of the third embodiment comprises, in order from the object side, −, F, +, S, +, C. As shown in FIG. 4, the objective optical system of the fourth embodiment comprises, in order from the object side, −, F, +, S, F, +, +. As shown in FIG. 5, the objective optical system of the fifth embodiment comprises, in order from the object side, −, F, +, F, S, +, +, C.

TABLE 2

Focal Length: 0.57631 F number: 4.992
Field of View: 112.2 degree

| S | R | D | Nd | Vd | Comment |
|---|---|---|---|---|---|
| Object | INF | 8 | 1 | | |
| 1 | INF | 0.2 | 1.9 | 35 | Autoclavable Optical Glass |
| 2 | 0.4939 | 0.2477 | 1 | | |
| 3 | INF | 0.5 | 1.494 | 75 | IR Cut Filter with Laser cut Multi-Layer Coating |
| 4 | INF | 0.03 | 1 | | |
| 5 | 1.8448 | 0.9078 | 1.816 | 46.62 | |
| 6 | −1.1932 | 0.03 | 1 | | |
| 7 | INF | 0.06 | 1 | | Aperture Stop |
| 8 | INF | 0.5 | 1.494 | 75 | IR Cut Filter with Laser cut Multi-Layer Coating |
| 9 | INF | 0.03 | 1 | | |
| 10 | 1.0192 | 0.6014 | 1.51633 | 64.14 | |
| 11 | −0.6831 | 0.2 | 1.92286 | 18.9 | |
| 12 | −1.9523 | 0.2131 | 1 | | |
| 13 | INF | 0.4 | 1.51633 | 64.14 | Cover Glass (anti-dust) |
| 14 | INF | 0.01 | 1.51 | 64.14 | Optical Cement |
| 15 | INF | 0.4 | 1.52 | 64.14 | CCD Cover Glass |
| 16 | INF | 0.01 | 1.56 | 64.14 | Optical Cement |
| 17 | INF | 0.019 | 1 | | |
| Image | INF | 0 | | | |

TABLE 3

Forcal Length: 0.60956 F number: 3.338
Field of View: 110.3 degree

| S | R | D | Nd | Vd | Comment |
|---|---|---|---|---|---|
| Object | INF | 12 | 1 | | |
| 1 | INF | 0.2 | 1.95 | 30 | Autoclavable Optical Glass |
| 2 | 0.4918 | 0.284 | 1 | | |
| 3 | INF | 0.62 | 1.514 | 75 | IR Cut Filter |
| 4 | INF | 0.067 | 1 | | |
| 5 | 1.6264 | 0.8858 | 1.7725 | 49.6 | |
| 6 | −1.2395 | 0.03 | 1 | | |
| 7 | INF | 0.06 | 1 | | Aperture Stop |
| 8 | 1.1794 | 0.7424 | 1.51633 | 64.14 | |
| 9 | −0.7151 | 0.2064 | 1.84666 | 23.78 | |
| 10 | −6.7749 | 0.3808 | 1 | | |
| 11 | INF | 0.4 | 1.51633 | 64.14 | Covere Glass (anti-dust) |
| 12 | INF | 0.01 | 1.51 | 64.14 | Optical Cement |
| 13 | INF | 0.4 | 1.52 | 64.14 | CCD Cover Glass |
| 14 | INF | 0.034 | 1 | | |
| Image | INF | 0 | | | |

TABLE 4

Focal Length: 0.95018 F number: 4.190
Field of View: 132.4 degree

| S | R | D | Nd | Vd | Comment |
|---|---|---|---|---|---|
| Object | INF | 14.3 | 1 | | |
| 1 | INF | 0.3 | 1.95 | 30 | Autoclavable Optical Glass |
| 2 | 0.7412 | 0.41 | 1 | | |
| 3 | INF | 0.4 | 1.52287 | 59.89 | Laser cut filter |
| 4 | INF | 0.0589 | 1 | | |
| 5 | 3.163 | 1.356 | 1.8061 | 40.92 | |
| 6 | −1.662 | 0.2545 | 1 | | |
| 7 | INF | 0.03 | 1 | | Aperture Stop |
| 8 | INF | 1 | 1.494 | 75 | IR Cut Filter |
| 9 | INF | 0.0687 | 1 | | |
| 10 | 2.2215 | 1.16 | 1.72916 | 54.68 | |
| 11 | −1.232 | 0.2187 | 1.92286 | 18.9 | |
| 12 | INF | 0.4787 | 1 | | |
| 13 | 2.9114 | 0.8 | 1.51633 | 64.14 | |
| 14 | INF | 0.01 | 1.51 | 63 | Optical Cement |
| 15 | INF | 0.4 | 1.6109 | 50.2 | CCD Cover Glass |
| 16 | INF | 0.01 | 1.52 | 63 | Optical Cement |
| 17 | INF | 0.02 | 1 | | |
| Image | INF | 0 | | | |

TABLE 5

Focal Length: 1.16211 F number: 12.523
Field of View: 114.7 degree

| S | R | D | Nd | Vd | Comment |
|---|---|---|---|---|---|
| Object | INF | 13 | 1 | | |
| 1 | INF | 0.34 | 1.9 | 35 | Autoclavable Optical Glass |
| 2 | 0.874 | 0.33 | 1 | | |
| 3 | INF | 0.31 | 1.514 | 75 | IR Cut Filter with Laser cut Multi-Layer Coating |
| 4 | INF | 0.09 | 1 | | |
| 5 | 1.392 | 0.68 | 1.84666 | 23.78 | |
| 6 | INF | 0.03 | 1 | | |
| 7 | INF | 0.31 | 1.514 | 75 | IR Cut Filter with Laser cut Multi-Layer Coating |
| 8 | INF | 0.03 | 1 | | Aperture Stop |
| 9 | INF | 0.45 | 1.72916 | 54.68 | |
| 10 | −2.942 | 0.12 | 1 | | |
| 11 | INF | 0.65 | 1.51633 | 64.14 | |
| 12 | −1.581 | 0.45 | 1 | | |
| 13 | INF | 1.15 | 1.51633 | 64.14 | Cover Glass (anti-dust) |
| 14 | INF | 0.01 | 1.51 | 64.1 | Optical Cement |
| 15 | INF | 0.8 | 1.52 | 64.1 | CCD Cover Glass |
| 16 | INF | 0.01 | 1.56 | 64.1 | Optical Cement |
| 17 | INF | 0 | 1 | | |
| Image | INF | 0 | | | |

Figure 6A:
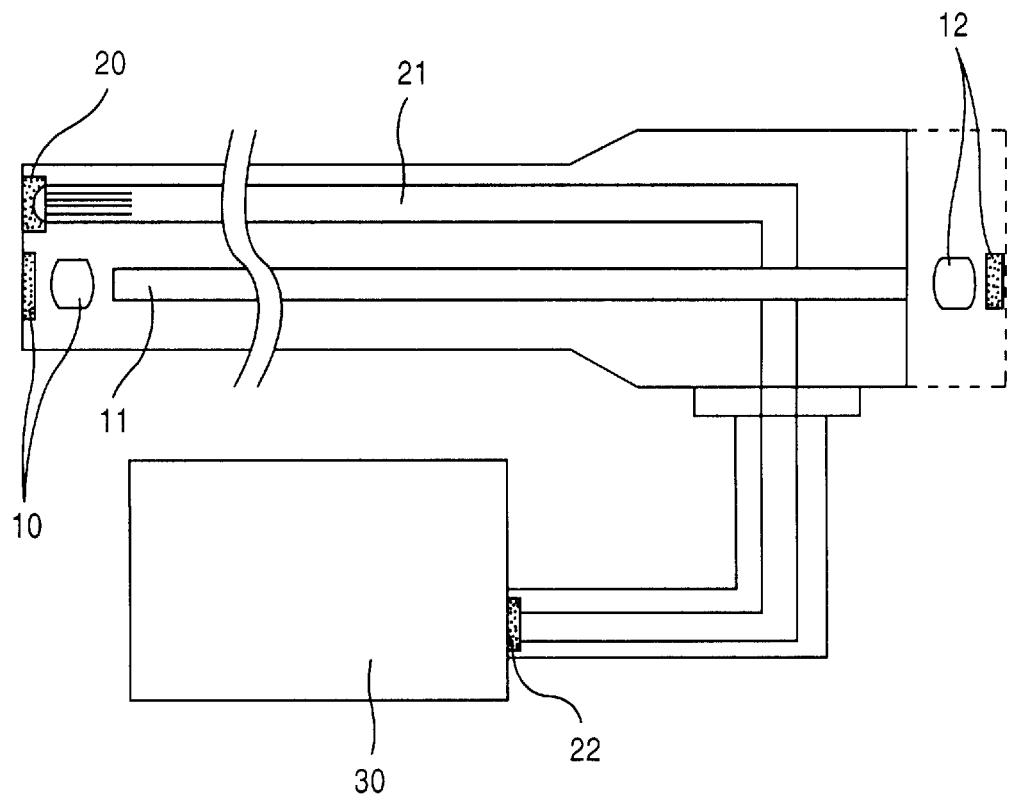
FIG. 6(a) is a general view showing an endoscope according to another embodiment of the present invention.

FIGS. 6(a) to (d) show a sixth embodiment. FIG. 6(a) is a general view showing an endoscope provided with an objective optical system 10 and an illuminating optical system 20 at a front end of an insertion section thereof. The insertion section has an image transmitting system 11 (i.e. signal transmitting means using a relay lens, an image guide fiber, or image pickup device) built-in. When the image transmitting system 11 is composed of a hard lens or a fiberscope using the relay lens or the image guide fiber, an ocular optical system 12 is additionally provided. Further, a connecting optical system is provided to connect a light source 30 to a light guide 21 for guiding light from the light source 30 to the illuminating optical system 20. All or a part of optical systems exposed to the outside air in the objective optical system 10, the illuminating optical system 20, the ocular optical system 12 and the connecting optical system 22 are formed of the composition having the improved sterilization durability. Thus, even if the whole of the endoscope is subjected to the sterilization treatment, a sufficient durability can be assured.

Each component will be described in detail. The details of the objective optical system 10 are the same as those described in conjunction with the first to fifth embodiments.

Figure 6B:
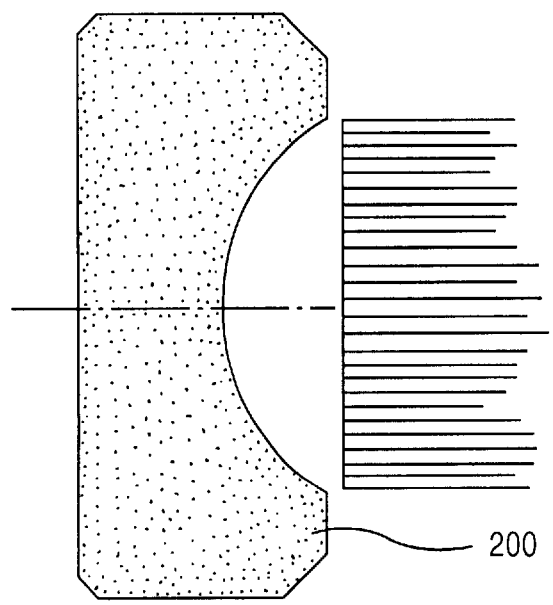
FIG. 6(b) shows an illuminating optical system using a negative lens, of the endoscope shown in FIG. 6(a).
Figure 6C:
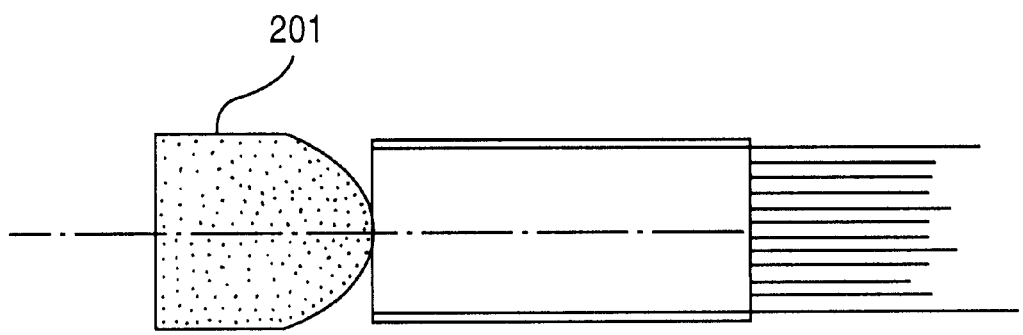
FIG. 6(c) shows an illuminating optical system using a positive lens, of the endoscope shown in FIG. 6(a).

The details of the illuminating optical system 20 are shown in FIGS. 6(b) and (c) in which FIGS. 6(b) shows an illuminating optical system 200 constructed by a negative lens and FIG. 6(c) shows an illuminating optical system 201 constructed by a positive lens. Each lens in FIGS. 6(b) and (c) may have a roughened surface or may include a light-diffusing portion to improve light distribution.

Figure 6D:
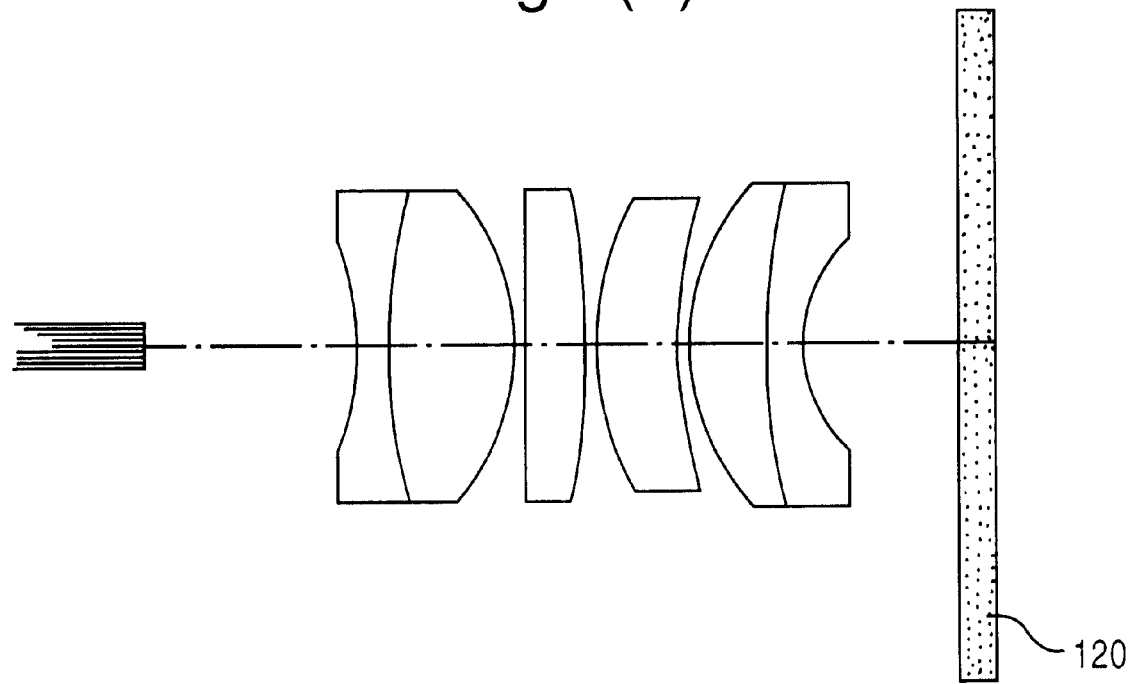
FIG. 6(d) shows an ocular optical system of the endoscope shown in FIG. 6(a).

The details of the ocular optical system 12 are shown in FIGS. 6(d). The ocular optical system 12 is composed of one modification of the Gaussian ocular lens system in which an image transmitted through the image guide fiber 11 is magnified to observe the image. A cover glass 120 located proximal to the observation side of the ocular optical system is formed of the composition having the improved sterilization durability.

Figure 7:
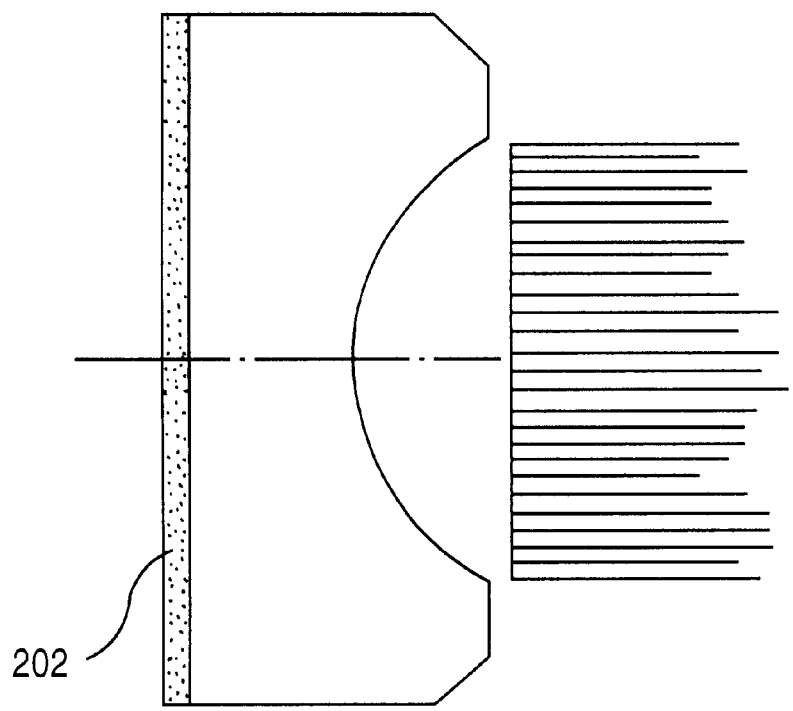
FIG. 7 shows an illuminating objective optical system having an outer surface formed of the composition of the present invention, according to another embodiment of the present invention.
Figure 8:
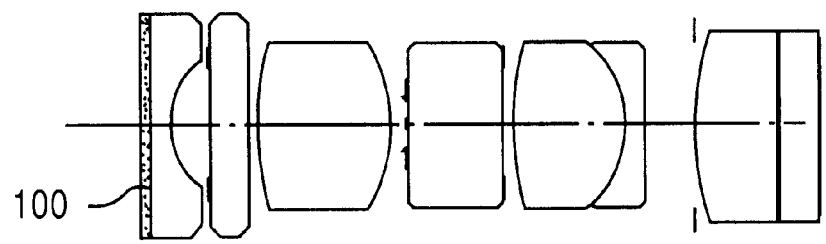
FIG. 8 shows an objective optical system having an outer surface formed of the composition of the present invention, according to another embodiment of the present invention.
Figure 9:
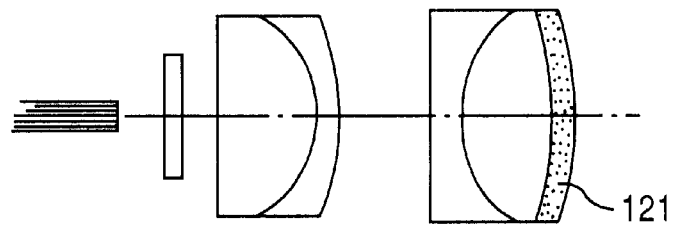
FIG. 9 shows an ocular optical system having an outer surface formed of the composition of the present invention, according to another embodiment of the present invention.

FIGS. 7 to 9 show seventh to ninth embodiments. In these embodiments, all or a part of the outer surface of the illuminating optical system 20, the objective optical system 10 and the ocular optical system 12 are formed of the composition having the improved sterilization durability. In this case, the composition having the improved sterilization durability is preferably formed in a thin film. Thus, even if the whole of the endoscope is subjected to the sterilization treatment, a sufficient durability can be assured. In the seventh embodiment shown in FIG. 7, the composition 202 having the improved sterilization durability is provided on the outer surface of the illuminating optical system 20. In the eighth embodiment shown in FIG. 8, the composition 100 having the improved sterilization durability is provided on the outer surface of the objective optical system 10. In the ninth embodiment shown in FIG. 9, the composition 121 having the improved sterilization durability is provided on the outer surface of the ocular optical system 12.

Figure 10:
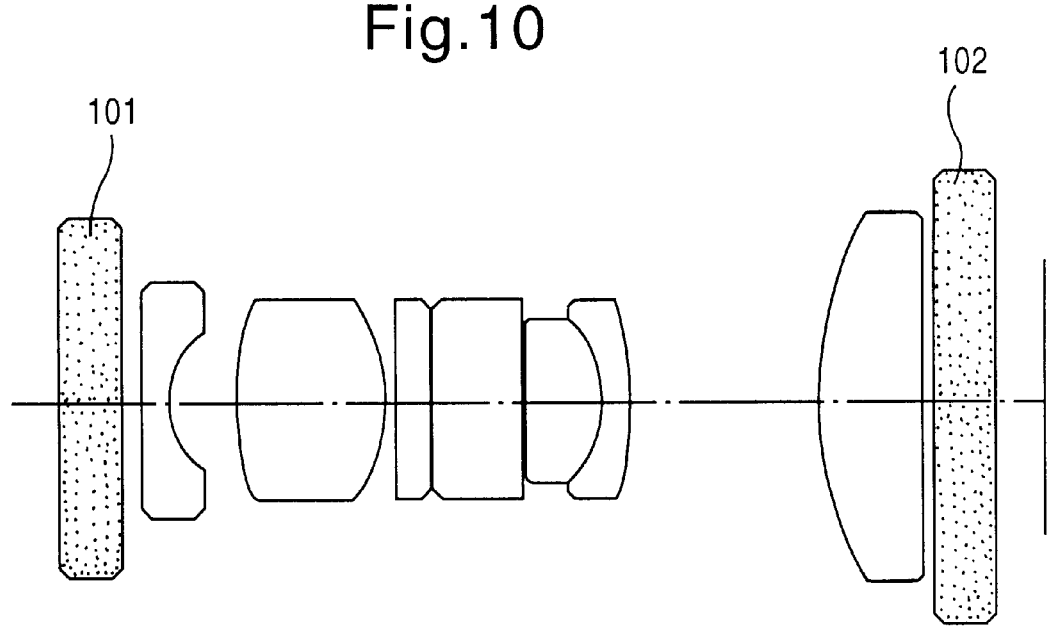
FIG. 10 shows an objective lens unit according to another embodiment of the present invention.

FIG. 10 shows another objective optical system according to a tenth embodiment. When it is difficult to assure the gas and pressure tightness of the overall endoscope, in order to yield the durability to the autoclave sterilization only to an objective lens unit, an optical element 101 located proximal to the object side of the objective lens unit and an optical element 102 located proximal to the image side of the objective lens unit are formed of the composition having the improved sterilization durability.

Figure 11:
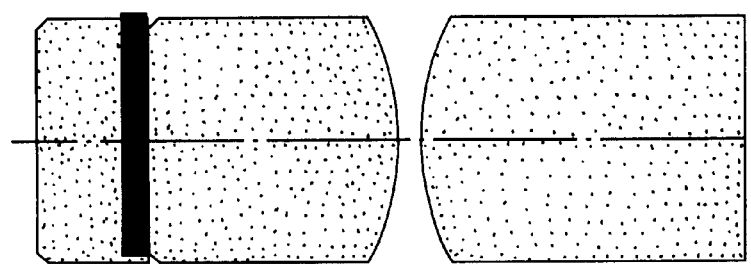
FIG. 11 shows an objective lens unit composed only of convex lenses, according to another embodiment of the present invention.

FIG. 11 shows an eleventh embodiment. As shown in FIG. 11, this embodiment comprises, in order from the object side, a cover glass having parallel surfaces and a pair of convex lenses. An objective lens unit is composed only of the pair of convex lenses. In this embodiment, all of the above optical elements are formed of the composition having the improved sterilization durability. An aperture diaphragm is provided between the cover glass having parallel surfaces and one of the convex lenses located proximal to the object side of the objective lens unit. When the aperture diaphragm has no sterilization durability, it is effective to seal the aperture diaphragm by the cover glass and the one of the convex lenses.

Figure 12:
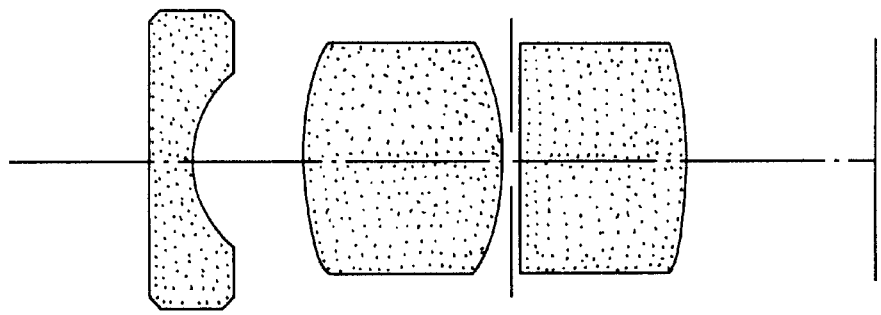
FIG. 12 shows a retrofocus type of objective lens unit according to another embodiment of the present invention.

FIG. 12 shows a twelfth embodiment. This embodiment is a so-called retrofocus type of objective lens unit consisting of a concave lens and a pair of convex lenses. In this embodiment, all of the above optical elements are formed of the composition having the improved sterilization durability.

Figure 13:
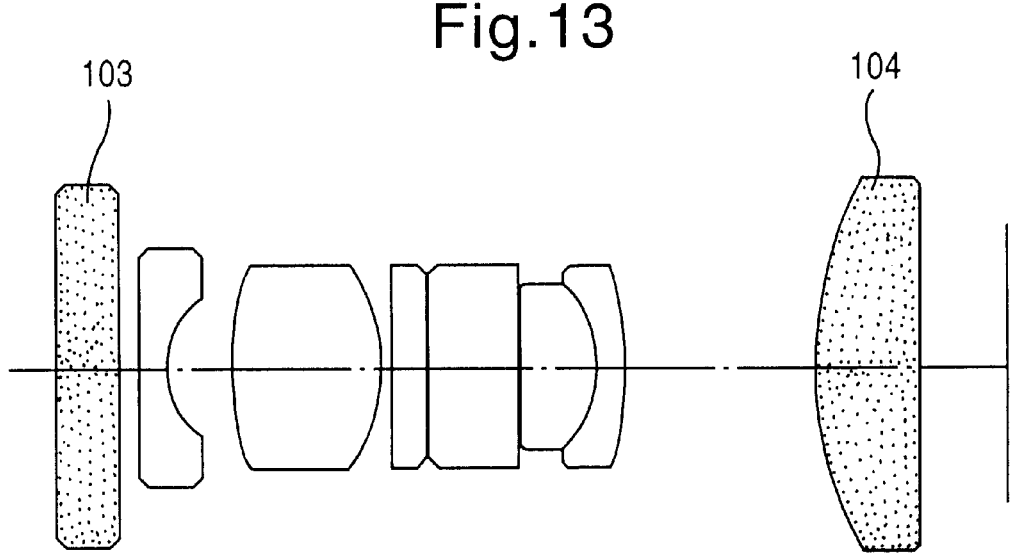
FIG. 13 shows an objective lens unit in which a convex lens is used as a lens located proximal to the image side of the objective lens unit, according to another embodiment of the present invention.

FIG. 13 shows a thirteenth embodiment. This embodiment is an objective lens unit including a convex lens serving as an optical element 104 located proximal to the image side of the objective lens unit. An optical element 103 located proximal to the object side of the objective lens unit and the optical element 104 located proximal to the image side of the objective lens unit are formed of the composition having the improved sterilization durability.

Figure 14:
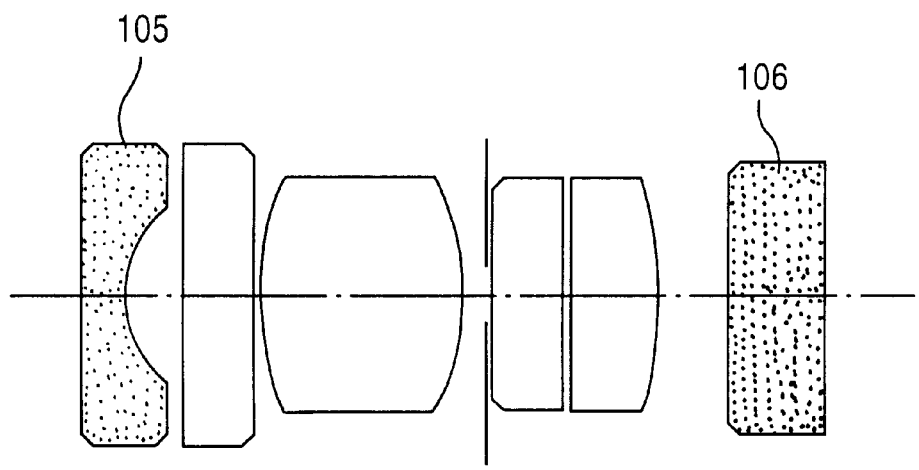
FIGS. 14 and 15 show objective lens units each having an infrared cut-off filter, according to other embodiments of the present invention, respectively.
Figure 15:
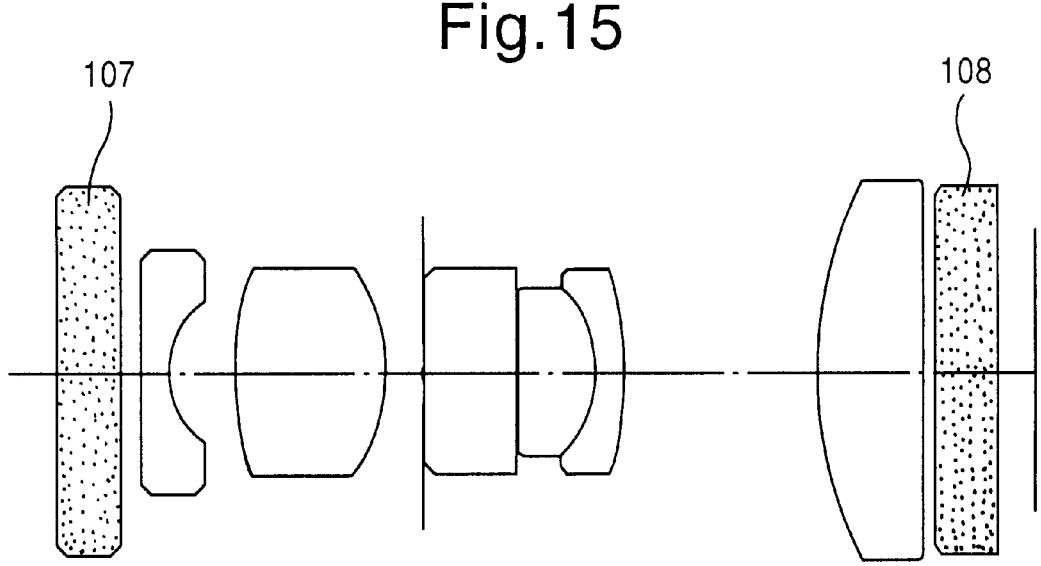

FIGS. 14 and 15 show fourteenth and fifteenth embodiments, respectively. In the fourteenth embodiment, an optical element 105 located proximal to the object side of the objective lens unit and an optical element 106 located proximal to the image side of the objective lens unit are formed of the composition having the improved sterilization durability. The optical element 106 located proximal to the image side of the objective lens unit is composed of an absorption type infrared cut-off filter or interference type infrared cut-off filter. The fifteenth embodiment is different in lens type from the fourteenth embodiment. In the fifteenth embodiment, an optical element 107 located proximal to the object side of the objective lens unit and an optical element 108 located proximal to the image side of the objective lens unit are formed of the composition having the improved sterilization durability. The optical elements 106 and 108 of the fourteenth and fifteenth embodiments located proximal to the image side of the objective lens unit may be commonly used as a dust-protection cover glass disposed in front of a CCD cover glass of the image pickup device unit.

Figure 16:
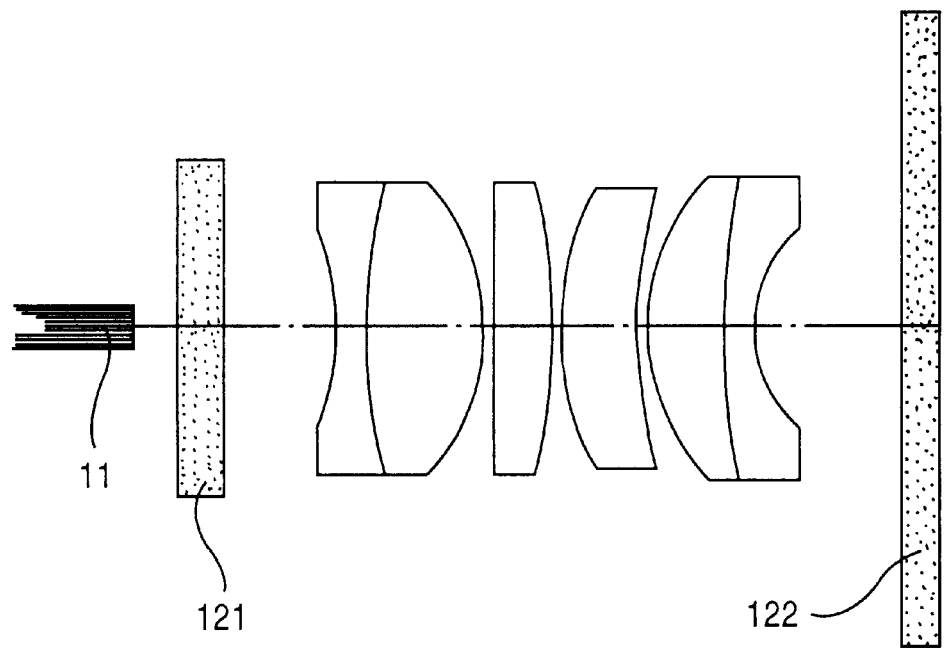
FIG. 16 shows an ocular lens unit according to another embodiment of the present invention.

FIG. 16 shows an ocular optical system according to a sixteenth embodiment. When it is difficult to assure the gas and pressure tightness of the overall endoscope, in order to yield the durability to the autoclave sterilization only to an ocular lens unit, the following stricture is employed. That is, the sixteenth embodiment comprises, in order from the object side, an image guide 11 and the ocular lens unit. An optical element 121 located proximal to the image guide side of the ocular lens unit and an optical element 122 located proximal to the observation side of the ocular lens unit are formed of the composition having the improved sterilization durability.

Figure 17:
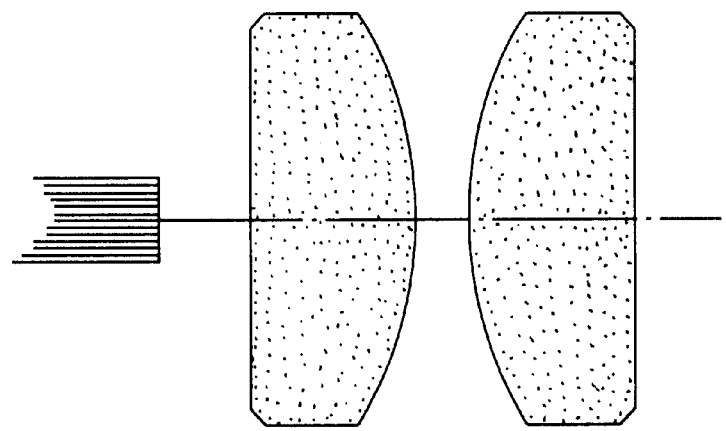
FIG. 17 shows a Ramsden type of ocular lens unit according to another embodiment of the present invention.

FIG. 17 shows another ocular optical system according to a seventeenth embodiment. In the seventeenth embodiment, all of optical elements are formed of the composition having the improved sterilization durability. This ocular lens unit is a Ramsden type of ocular lens unit which has a simplest structure without any bonded surface. Thus, this embodiment may be effectively used when an applied adhesive has insufficient sterilization durability. However, in the present invention, the lens unit is not limited to a particular type.

Figure 18:
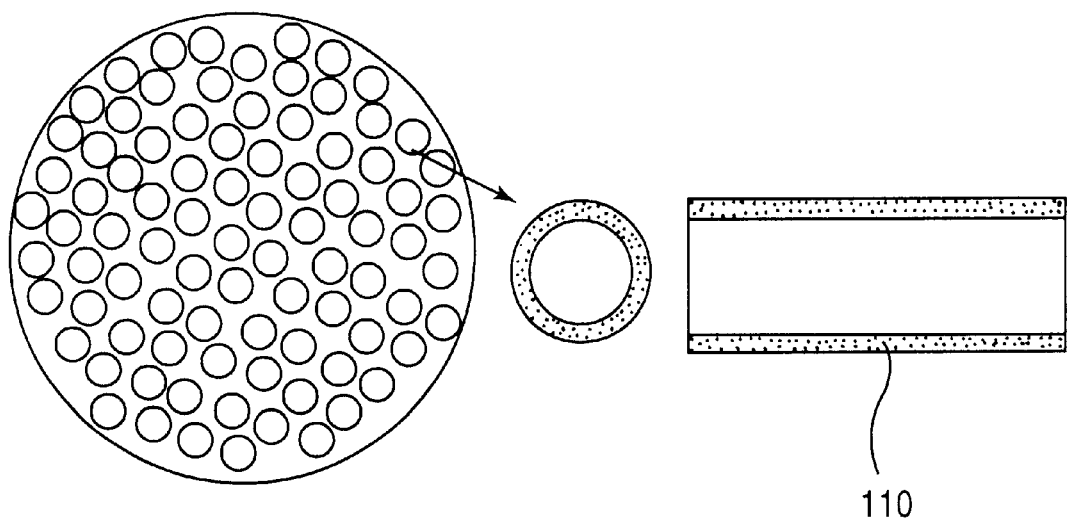
FIGS. 18 to 20 are end and sectional views showing image guides according to other embodiments of the present invention, respectively.
Figure 19:
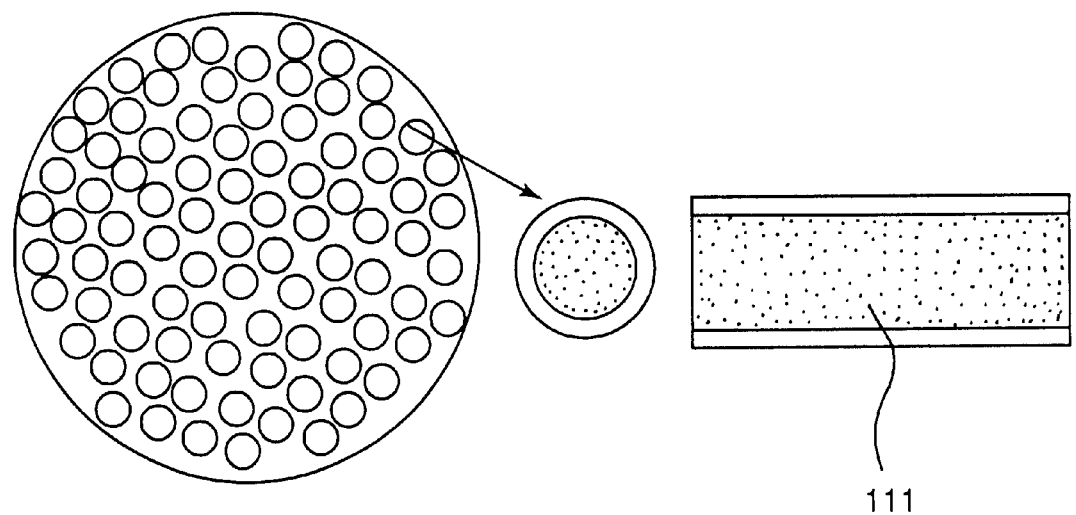
Figure 20:
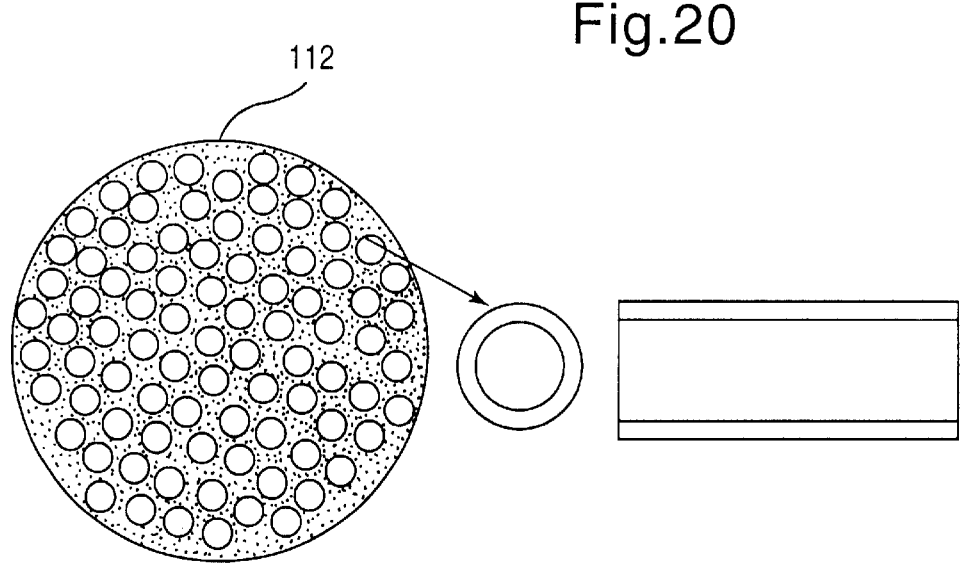

FIGS. 18 to 20 show various image guides according to eighteenth to twentieth embodiments, respectively. A part of each image guide of these embodiments is formed of the composition having the improved sterilization durability. Specifically, in the eighteenth embodiment, a clad 110 of the image guide is formed of the composition having the improved sterilization durability. In the nineteenth embodiment, a core 111 of the image guide is formed of the composition having the improved sterilization durability. In the twentieth embodiment, the outside section 112 of the clad 110 is formed of the composition having the improved sterilization durability.

Figure 21:
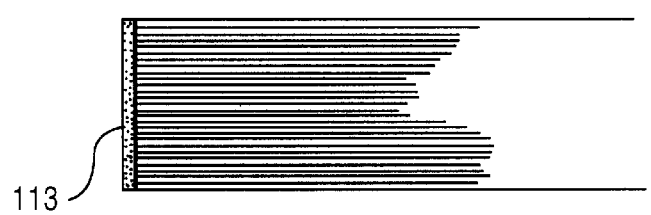
FIG. 21 shows an image guide having an incident end or outgoing end formed of the composition of the present invention, according to another embodiment of the present invention.

FIG. 21 shows a twenty-first embodiment. In this embodiment, an incident or outgoing end element 113 of an image guide is formed of the composition having the improved sterilization durability.

Figure 22:
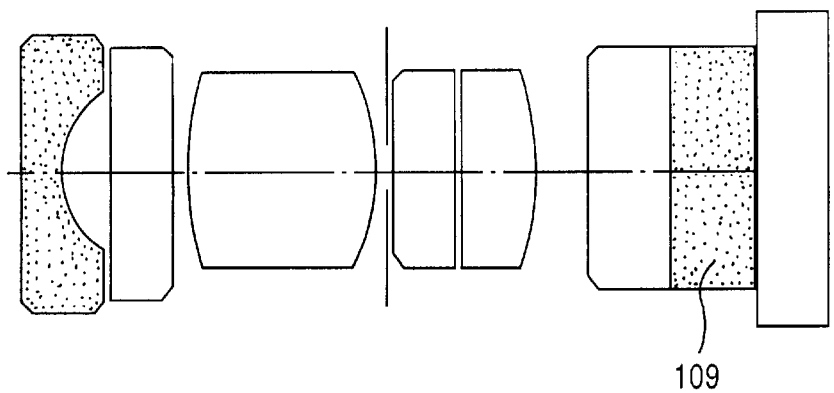
FIG. 22 shows an image pickup device according to another embodiment of the present invention, in which an optical element located proximal to the object side of the image pickup device is formed of the composition of the present invention.

FIG. 22 shows a twenty-second embodiment. This embodiment includes an image pickup device for imaging an object on the front end of the insertion section of the endoscope. An optical element 109 located proximal to the object side of the image pickup device is formed of the composition having the improved sterilization durability.

Figure 23:
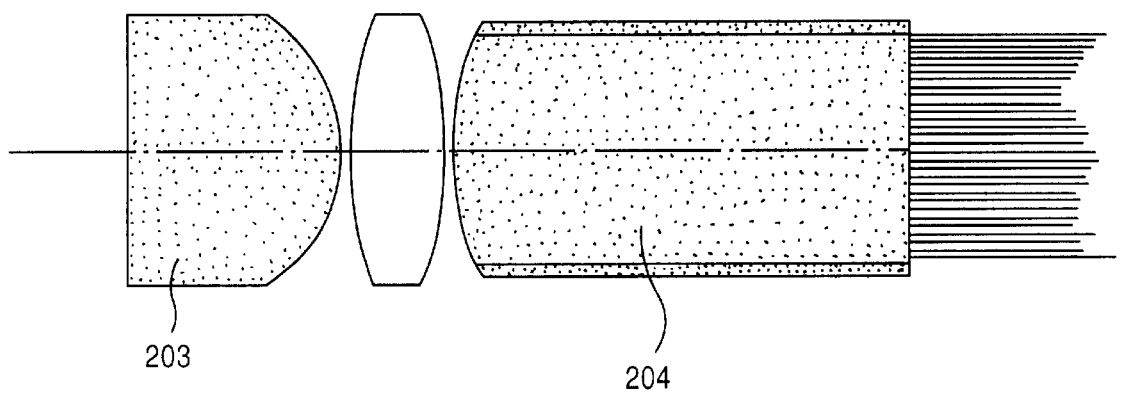
FIG. 23 shows an illuminating unit according to another embodiment of the present invention.

FIG. 23 shows a twenty-third embodiment. This embodiment includes an illuminating unit and a light guide, and an optical element 203 located proximal to the object side of the illuminating unit and an optical element 204 located proximal to the light guide side of the illuminating unit are formed of,the composition having the improved sterilization durability.

Figure 24:
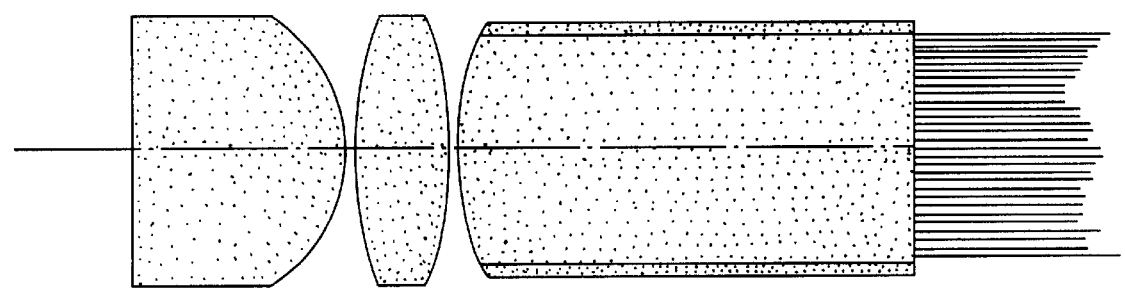
FIG. 24 shows an illuminating unit according to another embodiment of the present invention.

FIG. 24 shows a twenty-fourth embodiment. This embodiment includes an illuminating unit and a light guide, and all of optical elements of the illuminating unit are formed of the composition having the improved sterilization durability.

Figure 25:
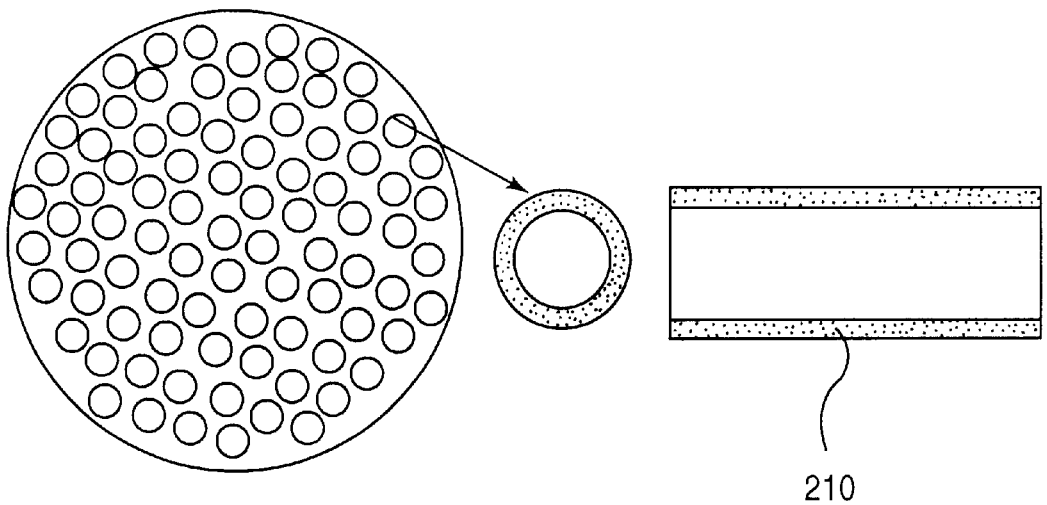
FIGS. 25 and 26 are end and sectional views showing light guides according to other embodiments of the present invention, respectively.
Figure 26:
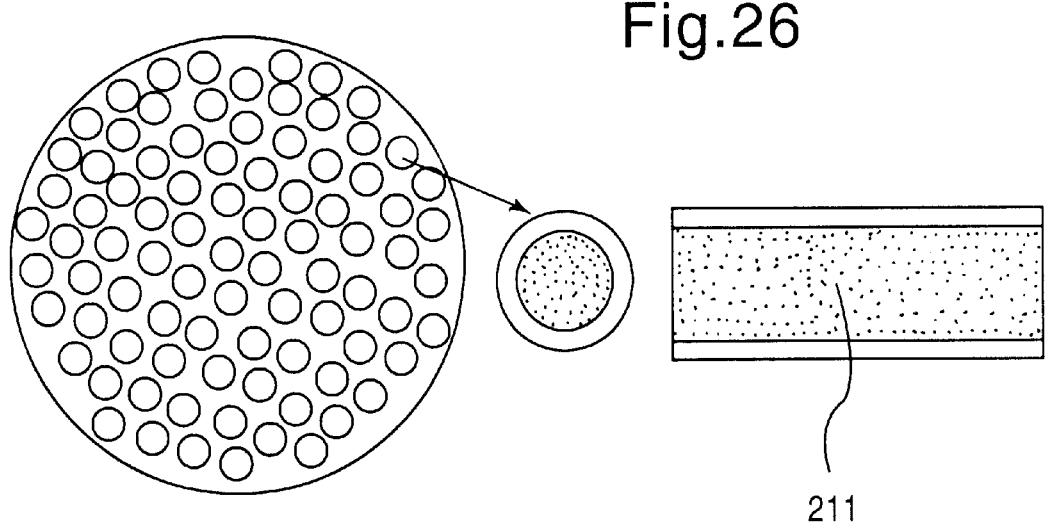

FIGS. 25 and 26 shows twenty-fifth and twenty-sixth embodiments, respectively. In these embodiments, a part of each light guide is formed of the composition having the improved sterilization durability. Specifically, in the twenty-fifth embodiment, a clad 210 of the light guide is formed of the composition having the improved sterilization durability. In the twenty-sixth embodiment, a core 211 of the light guide is formed of the composition having the improved sterilization durability.

Figure 27:
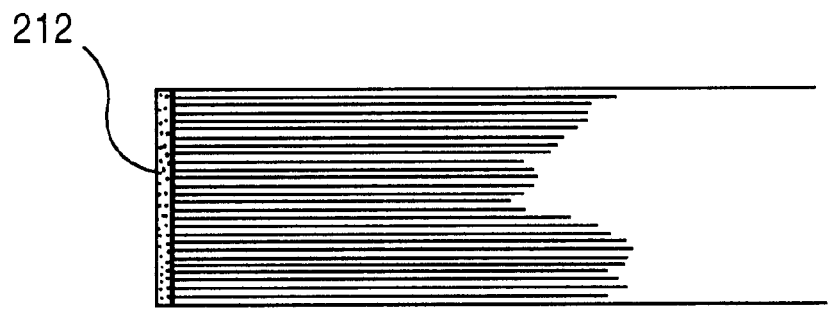
FIG. 27 shows a light guide having an incident end or an outgoing end formed of the composition of the present invention, according to another embodiment of the present invention.

FIG. 27 shows a twenty-seventh embodiment. In this embodiment, an incident or outgoing end element 212 of a light guide is formed of the composition having the improved sterilization durability.

Figure 28:
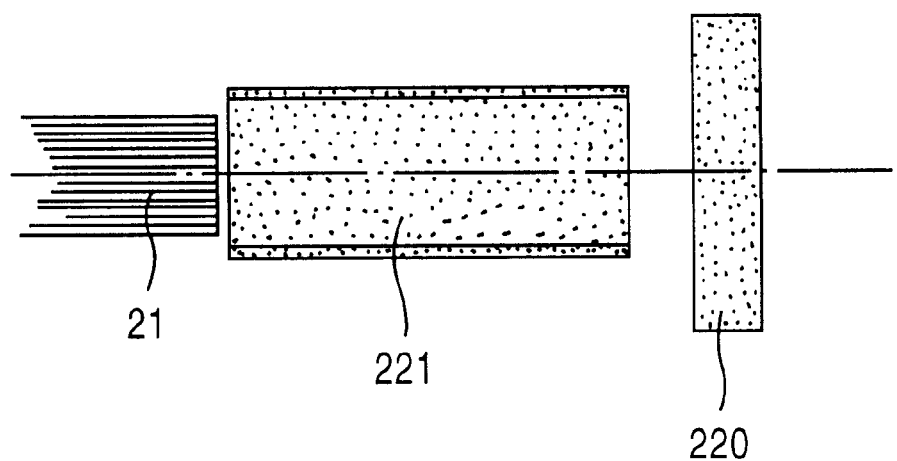
FIG. 28 shows a connecting optical system according to another embodiment of the present invention.

FIG. 28 shows a twenty-eighth embodiment. This embodiment includes a light source and a connecting optical system 22. The connecting optical system 22 is composed of an incident unit adjacent to a light guide 21, and an optical element 220 located proximal to the light source side of the incident unit or an optical element 221 located proximal to the light guide side of the incident unit is formed of the composition having the improved sterilization durability. Otherwise, all of the optical elements of the incident unit may be formed of the composition having the improved sterilization durability. Further, the optical element 221 of the incident unit may be a columnar rod-shaped optical element formed of the composition having the improved sterilization durability.

The invention has now been explained with reference to specific embodiments. Other embodiments will be apparent to those of ordinary skill in the art. Therefore, it is not intended that the invention be limited, except as indicated by the appended claims, which form a part of this invention description.

What is claimed is:

1. An endoscope using a composition having a durability to a sterilization treatment losing vapor under high temperature and pressure and capable of transmitting or absorbing light, said composition comprising:

a group A including at least either one of lanthanum oxide, gadolinium oxide, tantalum oxide and yttrium oxide, a total mol % of said group A being 25 mol % or more; and a group B including at least either one of boron oxide, silicon oxide and germanium oxide, a total mol % of said group B being 60 mol % or less, wherein an optical element disposed at an outer surface of an optical system of said endoscope is formed of said composition.

2. An endoscope as defined in claim 1, wherein said optical system includes an observation system and an illuminating system, wherein at least either one of an optical element disposed at the outer surface of said observation system and an optical element disposed at the outer surface of said illuminating system is formed of said composition.

3. An endoscope as defined in claim 1, wherein said optical system includes an observation system and an illuminating system, wherein all of an optical element disposed at the outer surface of said observation system and an optical element disposed at the outer surface of said illuminating system are formed of said composition.

4. An endoscope using a composition having a durability to a sterilization treatment using vapor under high temperature and pressure and capable of transmitting or absorbing light, said composition comprising:

a group A including at least either one of lanthanum oxide, gadolinium oxide, tantalum oxide and yttrium oxide, a total mol % of said group A being 25 mol % or more; and a group B including at least either one of boron oxide, silicon oxide and germanium oxide, a total mol % of said group B being 60 mol % or less, wherein a surface of an optical element disposed at an outer surface of an optical system of said endoscope is formed of said composition.

5. An endoscope as defined in claim 4, wherein said optical system includes an observation system and an illuminating system, wherein at least either one of a surface of an optical element disposed at the outer surface of said observation system and a surface of an optical element disposed at the outer surface of said illuminating system is formed of said composition.

6. An endoscope as defined in claim 4, wherein said optical system includes an observation system and an illuminating system, wherein all of a surface of an optical element disposed at the outer surface of said observation system and a surface of an optical element disposed at the outer surface of said illuminating system are formed of said composition.

7. An endoscope using a composition having a durability to a sterilization treatment using vapor under high temperature and pressure and capable of transmitting or absorbing light, said composition comprising:

a group A including at least either one of lanthanum oxide, gadolinium oxide, tantalum oxide and yttrium oxide, a total mol % of said group A being 25 mol % or more; and a group B including at least either one of boron oxide, silicon oxide and germanium oxide, a total mol % of said group B being 60 mol % or less, which includes an objective lens unit for imaging an object on a front end of an insertion section of said endoscope, wherein an optical element located proximal to the object side of said objective lens unit and an optical element located proximal to the image side of said objective lens unit are formed of said composition.

8. An endoscope as defined in claim 7, wherein all of optical elements of said objective lens unit are formed of said composition.

9. An endoscope as defined in claim 7, wherein said optical element located proximal to the image side of said objective lens unit is a convex lens.

10. An endoscope as defined in claim 7, wherein said optical element located proximal to the image side of said objective lens unit is either one of an absorption type infrared cut-off filter and an interference type infrared cut-off filter.

11. An endoscope using a composition having a durability to a sterilization treatment using vapor under high temperature and pressure and capable of transmitting or absorbing light, said composition comprising:

a group A including at least either one of lanthanum oxide, gadolinium oxide, tantalum oxide and yttrium oxide, a total mol % of said group A being 25 mol % or more; and a group B including at least either one of boron oxide, silicon oxide and germanium oxide, a total mol % of said group B being 60 mol % or less, which includes, in order from the object side of said endoscope, an image guide and an ocular lens unit, wherein an optical element located proximal to the image guide of said ocular lens unit and an optical element located proximal to the observation side of said ocular lens unit are formed of said composition.

12. An endoscope as defined in claim 11, wherein all of optical elements of said ocular lens unit are formed of said composition.

13. An endoscope as defined in claim 11, wherein at least a part of said image guide is formed of said composition.

14. An endoscope using a composition having a durability to a sterilization treatment using vapor under high temperature and pressure and capable of transmitting or absorbing light, said composition comprising:

a group A including at least either one of lanthanum oxide, gadolinium oxide, tantalum oxide and yttrium oxide, a total mol % of said group A being 25 mol % or more; and a group B including at least either one of boron oxide, silicon oxide and germanium oxide, a total mol % of said group B being 60 mol % or less, which includes an image pickup device for imaging an object on a front end of an insertion section of said endoscope, wherein an optical element located proximal to the object side of said image pickup device is formed of said composition.

15. An endoscope using a composition having a durability to a sterilization treatment using vapor under high temperature and pressure and capable of transmitting or absorbing light, said composition comprising:

a group A including at least either one of lanthanum oxide, gadolinium oxide, tantalum oxide and yttrium oxide, a total mol % of said group A being 25 mol % or more; and a group B including at least either one of boron oxide, silicon oxide and germanium oxide, a total mol % of said group B being 60 mol % or less, which includes, in order from the object side at a front end of an insertion section of said endoscope, an illuminating unit and a light guide, wherein an optical element located proximal to the object side of said illuminating unit and an optical element located proximal to the light guide side of said illuminating unit are formed of said composition.

16. An endoscope as defined in claim 15, wherein all of optical elements of said illuminating unit are formed of said composition.

17. An endoscope as defined in claim 15, wherein at least a part of said light guide is formed of said composition.

18. An endoscope using a composition having a durability to a sterilization treatment using vapor under high temperature and pressure and capable of transmitting or absorbing light, said composition comprising:

a group A including at least either one of lanthanum oxide, gadolinium oxide, tantalum oxide and yttrium oxide, a total mol % of said group A being 25 mol % or more; and a group B including at least either one of boron oxide, silicon oxide and germanium oxide, a total mol % of said group B being 60 mol % or less, which includes, in order from the light source side of said endoscope, an incident unit and a light guide, wherein an optical element located proximal to the light source side of said incident unit and an optical element located proximal to the light guide side of said incident unit are formed of said composition.

19. An endoscope as defined in claim 18, wherein all of optical elements of said incident unit are formed of said composition.

20. An endoscope as defined in claim 18, said incident unit includes a columnar rod-shaped optical element, wherein said rod-shaped optical element is formed of said composition.

* * * * *